United States Patent
Ni et al.

(10) Patent No.: US 11,542,479 B2
(45) Date of Patent: Jan. 3, 2023

(54) ALCOHOL DEHYDROGENASE MUTANT AND USE THEREOF

(71) Applicant: JIANGNAN UNIVERSITY, Wuxi (CN)

(72) Inventors: Ye Ni, Wuxi (CN); Wei Dai, Wuxi (CN); Guochao Xu, Wuxi (CN); Jieyu Zhou, Wuxi (CN); Ruizhi Han, Wuxi (CN); Jinjun Dong, Wuxi (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 57 days.

(21) Appl. No.: 15/734,556

(22) PCT Filed: May 13, 2020

(86) PCT No.: PCT/CN2020/089961
§ 371 (c)(1),
(2) Date: Dec. 2, 2020

(87) PCT Pub. No.: WO2021/103432
PCT Pub. Date: Jun. 3, 2021

(65) Prior Publication Data
US 2021/0363500 A1    Nov. 25, 2021

(30) Foreign Application Priority Data
Nov. 26, 2019 (CN) .......................... 201911175255.0

(51) Int. Cl.
| | |
|---|---|
| *C12N 9/04* | (2006.01) |
| *C12P 7/22* | (2006.01) |
| *C12P 17/12* | (2006.01) |
| *C12N 1/21* | (2006.01) |
| *C12N 15/53* | (2006.01) |
| *C12N 9/02* | (2006.01) |

(52) U.S. Cl.
CPC ......... *C12N 9/0006* (2013.01); *C12N 9/0008* (2013.01); *C12N 9/0093* (2013.01); *C12P 7/22* (2013.01); *C12P 17/12* (2013.01); *C12Y 101/01001* (2013.01); *C12Y 101/01006* (2013.01); *C12Y 101/01027* (2013.01); *C12Y 101/01047* (2013.01); *C12Y 120/01001* (2013.01)

(58) Field of Classification Search
None
See application file for complete search history.

(56) References Cited

U.S. PATENT DOCUMENTS 10,865,390 B2 * 12/2020 Ni .................... C12N 9/0006

FOREIGN PATENT DOCUMENTS

| CN | 105936895 A | * | 9/2016 |
|---|---|---|---|
| CN | 108359649 A | | 8/2018 |
| CN | 109402076 A | | 3/2019 |
| CN | 110982799 A | | 4/2020 |

OTHER PUBLICATIONS

Xu et al., Hydraclassiled Combinatorial Saturation Mutagenesis: Reshaping Substrate Binding Pockets of KpADH for Enantioselective Reduction of Bulky-Bulky Ketones, ACA Catalysis, vol. 8, No. 9, pp. 8336-8345 (Aug. 13, 2018).
Zhou et al., Structural Insight into Enantioselective Inversion of an Alcohol Dehydrogenase Reveals a "Polar Gate" in Stereorecognition of Diaryl Ketones, J. Am. Chem. Soc. 2018, 140, 12645-12654 (Sep. 24, 2018).

* cited by examiner

*Primary Examiner* — Robert B Mondesi
*Assistant Examiner* — Todd M Epstein
(74) *Attorney, Agent, or Firm* — SZDC Law P.C.

(57) ABSTRACT

The invention discloses an alcohol dehydrogenase mutant and use thereof. The alcohol dehydrogenase mutant of the present invention has high thermal stability and enables high catalytic efficiency and high conversion rate (i.e. space time yield) in the asymmetric reduction of prochiral diaryl ketones to produce chiral diaryl alcohols. Therefore, the alcohol dehydrogenase mutant of the present invention has extremely high prospect of application in the production of chiral diaryl alcohols, such as (S)-(4-chlorophenyl)-(pyridin-2-yl)-methanol, (R)-(4-chlorophenyl)-(pyridin-2-yl)-methanol.

9 Claims, 4 Drawing Sheets
Specification includes a Sequence Listing.

ALCOHOL DEHYDROGENASE MUTANT AND USE THEREOF

This application is the National Stage Application of PCT/CN2020/089961, filed on May 13, 2020, which claims priority to Chinese Patent Application No. 201911175255.0, filed on Nov. 26, 2019, which is incorporated by reference for all purposes as if fully set forth herein.

FIELD OF THE INVENTION

The present invention relates to the technical field of enzyme engineering and microbial engineering, and particularly to an alcohol dehydrogenase mutant and use thereof.

DESCRIPTION OF THE RELATED ART

Chiral diaryl alcohols are an important class of chiral compounds that can be used to synthesize various drugs such as betahistine and rotoxamine. Therefore, chiral diaryl alcohols have a wide scope of applications in the field of medicine.

At present, the method for producing chiral diaryl alcohols mainly includes chemical asymmetric synthesis. In this method, by using a prochiral diaryl ketone as a raw material, and trans-$RuCl_2$[(R)-xylbinap][(R)-daipen], (S)-[Ru(BINAP)$Cl_2$]$_2$($NE_3$), or (S,S)-6-CHOONa as a catalyst, or chiral BINAL-H as a chiral reducing agent, asymmetric reduction is performed under certain conditions (high pressure) to obtain a chiral diaryl alcohol (see "C. Y. Chen, et al., Org. Lett., 2003, 5, 5039-5042", "Zhao Zhiquan et al., Chinese Journal of Pharmaceutical Industry, 2006, 37, 726-727", and "B. G. Wang, et al, Org. Lett., 2017, 19, 2094-2097"; and Patent Application Publication Nos. CN101848893A and CN103121966A).

However, the catalysts or chiral reducing agents used in the chemical asymmetric synthesis are expensive, the reaction requires high pressure and the synthesized product has low optical purity, which are not conducive to industrial production, and cannot meet the requirement of medicines for optical purity.

Enzymatic asymmetric reduction refers to a method of producing a chiral diaryl alcohol by asymmetric reduction of a prochiral diaryl ketone as a raw material and an enzyme as a catalyst. Compared with the chemical asymmetric synthesis, the enzymatic asymmetric reduction has the advantages of mild reaction conditions, low cost and high optical purity of the synthesized product, thus meeting "sustainable development", "green chemistry", "environmentally friendly manufacturing" and other industrial development goals. Therefore, the production of chiral diaryl alcohols by enzymatic asymmetric reduction is of great significance to the large-scale industrial production of chiral diaryl alcohols and the wide use of chiral diaryl alcohols in the field of medicine.

The existing enzymes that can be used for asymmetric reduction of prochiral diaryl ketones to produce chiral diaryl alcohols are mainly alcohol dehydrogenase (ADH, EC 1.1.1.1). However, most of the alcohol dehydrogenase enzymes have low thermal stability and the $T_{50}^{15}$ is below 50° C. (see: "Min Li, et al., Applied and Environmental Microbiology., 2017, 83, 12, e00603-17", and "Xumin Gong, et al, ACS Catalysis, 2019, 9, 1, 147-153"). This makes the alcohol dehydrogenase easier to deactivate at industrial production temperatures, Furthermore, the conversion rate in the production of chiral diaryl alcohols by the asymmetric reduction of prochiral diaryl ketones by alcohol dehydrogenase is low, the space time yield is low, and S/C is less high (see: "Xumin Gong, et al, ACS Catalysis, 2019, 9, 1, 147-153", and "Jieyu Zhou, et al, J. Am. Chem. Soc. 2018, 140, 12645-12654"), which greatly hinders the industrialization progress of producing chiral diaryl alcohols by enzymatic asymmetric reduction.

Therefore, there is an urgent need to develop an alcohol dehydrogenase with high thermal stability and enabling high conversion efficiency in the asymmetric reduction of prochiral diaryl ketones to produce chiral diaryl alcohols, to realize the large-scale industrial production of chiral diaryl alcohols and the wide use of chiral diaryl alcohols in the field of medicine.

SUMMARY OF THE INVENTION

A technical problem to be solved by the present invention is to provide an alcohol dehydrogenase (ADH, EC 1.1.1.1) with high thermal stability and enabling high conversion efficiency in the asymmetric reduction of prochiral diaryl ketones to produce chiral diaryl alcohols.

To solve the above technical problem, the present invention provides an alcohol dehydrogenase mutant, which is obtained by mutating lysine at position 36, threonine at position 132, asparagine at position 159, lysine at position 210, threonine at position 248 and/or glutamine at position 272 in a starting amino acid sequence as shown in SEQ ID NO: 1 of alcohol dehydrogenase.

Alternatively, the alcohol dehydrogenase mutant is obtained by mutating lysine at position 36, threonine at position 132, asparagine at position 159, lysine at position 210, threonine at position 248, glutamine at position 272, glutamine at position 136, phenylalanine at position 161, serine at position 196, glutamate at position 214 and serine at position 237 in a starting amino acid sequence as shown in SEQ ID NO: 1 of alcohol dehydrogenase.

In an embodiment of the present invention, the alcohol dehydrogenase mutant is obtained by mutating lysine at position 36 to isoleucine, threonine at position 132 to aspartate, asparagine at position 159 to aspartate, lysine at position 210 to glutamate, threonine at position 248 to alanine and/or glutamine at position 272 to leucine in a starting amino acid sequence as shown in SEQ ID NO: 2 of alcohol dehydrogenase.

Alternatively, the alcohol dehydrogenase mutant is obtained by mutating lysine at position 36 to isoleucine, threonine at position 132 to aspartate, asparagine at position 159 to aspartate, lysine at position 210 to glutamate, threonine at position 248 to alanine, glutamine at position 272 to leucine, glutamine at position 136 to asparagine, phenylalanine at position 161 to valine, serine at position 196 to glycine, glutamate at position 214 to glycine, and serine at position 237 to cysteine in a starting amino acid sequence as shown in SEQ ID NO: 2 of alcohol dehydrogenase.

The present invention also provides a gene encoding the alcohol dehydrogenase mutant.

The present invention further provides a recombinant plasmid carrying the gene.

In an embodiment of the present invention, the vector of the recombinant plasmid is pET-28a(+) plasmid, pET-28b(+) plasmid or pET-20b(+) plasmid.

The present invention also provides a host cell carrying the gene or the recombinant plasmid.

In an embodiment of the present invention, the host cell is a bacterial cell, a fungal cell, a plant cell or an animal cell.

In an embodiment of the present invention, the host cell is a bacterial cell.

In an embodiment of the present invention, the host cell is *E. coli* cells.

In an embodiment of the present invention, the host cell is *E. coli* BL21(DE3) cells.

The present invention also provides a method for producing the alcohol dehydrogenase mutant, which comprises the steps of inoculating the host cells into a fermentation medium for fermentation to obtain a fermentation broth; centrifuging the fermentation broth to collect the bacterial cells; homogenizing the bacterial cells and centrifuging, to obtain a cell homogenate supernatant; and extracting the cell homogenate supernatant to obtain the alcohol dehydrogenase mutant.

The present invention also provides a method for producing a chiral diaryl alcohol. The method comprises adding the alcohol dehydrogenase mutant to a reaction system containing a prochiral diaryl ketone for reaction to obtain a reaction solution; and extracting the reaction solution to obtain a chiral diaryl alcohol.

In an embodiment of the present invention, the reaction system further contains a coenzyme and a coenzyme circulation system. The coenzyme circulation system comprises D-glucose and a glucose dehydrogenase, or a phosphite and a phosphite dehydrogenase, or a formate and a formate dehydrogenase, or a lactate and a lactate dehydrogenase, or glycerol and a glycerol dehydrogenase.

In an embodiment of the present invention, the coenzyme circulation system comprises D-glucose and a glucose dehydrogenase.

In an embodiment of the present invention, the coenzyme is $NADP^+$, NADPH, $NAD^+$ and/or NADH.

In an embodiment of the present invention, the alcohol dehydrogenase mutant is added to the reaction system in an amount of 1-10 kU/L.

In an embodiment of the present invention, the concentration of the prochiral diaryl ketone in the reaction system is 100-500 mmol/L.

In an embodiment of the present invention, the concentration of the coenzyme in the reaction system is 0.1-1 mmol/L.

In an embodiment of the present invention, the concentration of the glucose dehydrogenase in the reaction system is 1-10 kU/L.

In an embodiment of the present invention, the concentration of D-glucose in the reaction system is 20-1000 mmol/L.

In an embodiment of the present invention, the reaction system is a buffer containing a prochiral diaryl ketone, a coenzyme and a coenzyme circulation system.

In an embodiment of the present invention, the buffer is a phosphate buffer.

In an embodiment of the present invention, the concentration of the phosphate buffer is 0.1-0.2 mol/L.

In an embodiment of the present invention, the temperature of the reaction is 30-35° C., and the pH is 6-8.

In an embodiment of the present invention, the prochiral diaryl ketone is (4-chlorophenyl)-(pyridin-2-yl)-methanone, phenyl-2-pyridinylmethanone, 4-fluorodiphenylmethanone or 4-chlorodiphenylmethanone.

In an embodiment of the present invention, when the prochiral diaryl ketone is (4-chlorophenyl)-(pyridin-2-yl)-methanone, the chiral diaryl alcohol is (4-chlorophenyl)-(pyridin-2-yl)-methanol; when the prochiral diaryl ketone is phenyl-2-pyridinylmethanone, the chiral diaryl alcohol is phenyl-2-pyridinylmethanol; when the prochiral diaryl ketone is 4-fluorodiphenylmethanone, the chiral diaryl alcohol is 4-fluorodiphenylmethanol; and when the prochiral diaryl ketone is 4-chlorodiphenylmethanone, the chiral diaryl alcohol is 4-chlorodiphenylmethanol.

The present invention also provides use of the alcohol dehydrogenase mutant, the gene, the recombinant plasmid, the host cell in the production of a chiral diaryl alcohol.

In an embodiment of the present invention, the chiral diaryl alcohol is (4-chlorophenyl)-(pyridin-2-yl)-methanol, phenyl-2-pyridinylmethanone, 4-fluorodiphenylmethanone, or 4-chlorodiphenylmethanone.

In an embodiment of the present invention, the chiral diaryl alcohol is (S)-(4-chlorophenyl)-(pyridin-2-yl)-methanol or (R)-(4-chlorophenyl)-(pyridin-2-yl)-methanol.

(1) The alcohol dehydrogenase mutant of the present invention has high thermal stability, where the mutant MS has a $T_{50}^{15}$ and $E_d$ value of up to 45.8° C. and 968.26 kJ/mol respectively, which are 3.8° C. and 11.19 kJ/mol higher than those of the wild type. The mutant M63 has a $T_{50}^{15}$ and $E_d$ value of up to 53.1° C. and 989.13 kJ/mol respectively, which are 11.1° C. and 32.06 kJ/mol higher than those of the wild type. The mutant M64 has a $T_{50}^{15}$ and $E_d$ value of up to 51.5° C. and 984.14 kJ/mol, respectively, which are 9.5° C. and 27.07 kJ/mol higher than those of the wild type.

(2) The alcohol dehydrogenase mutant of the present invention enables a high conversion efficiency in the production of chiral diaryl alcohols by the asymmetric reduction of prochiral diaryl ketones, where the conversion efficiency (i.e. space time yield) in the production of chiral diaryl alcohols by the asymmetric reduction of prochiral diaryl ketones by the mutant M64 is as high as 651 g/(L·d), while the conversion rate by the wild type under the same conditions is less than 25%.

(3) The alcohol dehydrogenase mutant of the present invention has a high catalytic efficiency in the production of chiral diaryl alcohols by asymmetric reduction of prochiral diaryl ketones, where the catalytic efficiency of the mutant M63 in the production of chiral diaryl alcohols by the asymmetric reduction of prochiral diaryl ketones is 27.47 $s^{-1} \cdot mM^{-1}$, which is 1.3 times that of the wild type; and the catalytic efficiency of the mutant M64 in the production of chiral diaryl alcohols by the asymmetric reduction of prochiral diaryl ketones is 20.27 $s^{-1} \cdot mM^{-1}$, which is 1.37 times that of the control mutant S5.

(4) Wild-type alcohol dehydrogenase can asymmetrically reduce prochiral (4-chlorophenyl)-(pyridin-2-yl)-methanone to produce (R)-(4-chlorophenyl)-(pyridin-2-yl)-methanol, with an e.e. value of up to 87.1% (R). The alcohol dehydrogenase mutant of the present invention has inverse stereoselectivity in the asymmetric reduction of chiral aromatic ketones to produce chiral diaryl alcohols, where the mutant M64 can asymmetrically reduce prochiral (4-chlorophenyl)-(pyridin-2-yl)-methanone to produce (S)-(4-chlorophenyl)-(pyridin-2-yl)-methanol with an e.e. value of up to 97.6% (S).

(5) The alcohol dehydrogenase mutant of the present invention has high thermal stability and enables high catalytic efficiency and high conversion efficiency (i.e. space time yield) in the asymmetric reduction of prochiral diaryl ketones to produce chiral diaryl alcohols. Therefore, the alcohol dehydrogenase mutant of the present invention has extremely high prospect of application in the production of (S)-(4-chlorophenyl)-(pyridin-2-yl)-methanol, (R)-(4-chlorophenyl)-(pyridin-2-yl)-methanol and other chiral diaryl alcohols.

Marker; and Lanes 1-64: enzymatically cleaved products of recombinant plasmid pET28a-KpADH-1 to recombinant plasmid pET28a-KpADH-64.

Figure 1:
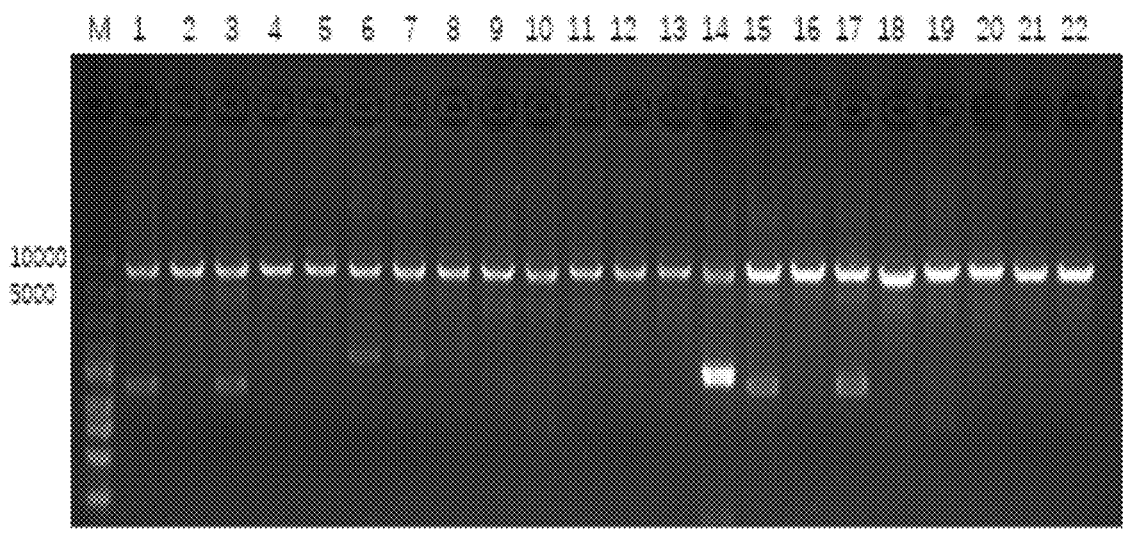
FIGS. 1, 2, 3, and 4 are electrophoretograms of recombinant plasmids obtained by PCR amplification, where M.
Figure 2:
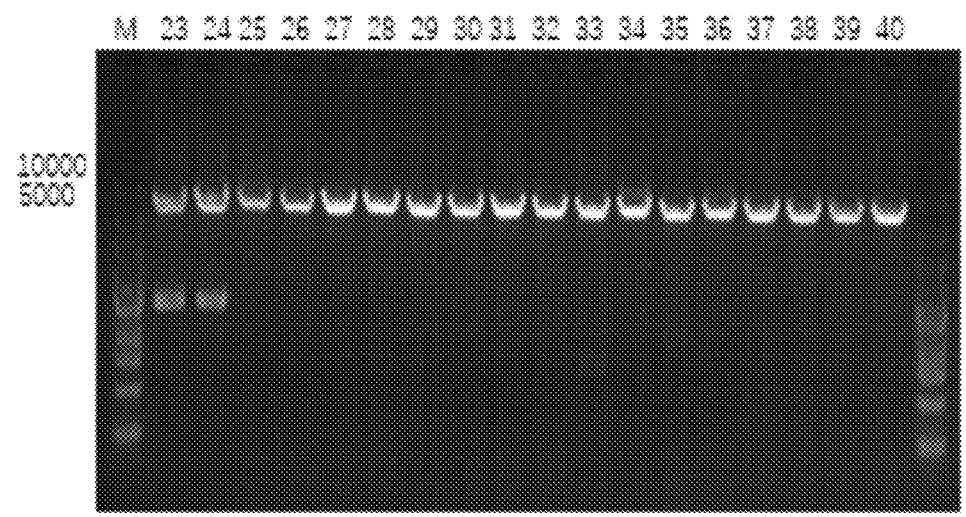
Figure 3:
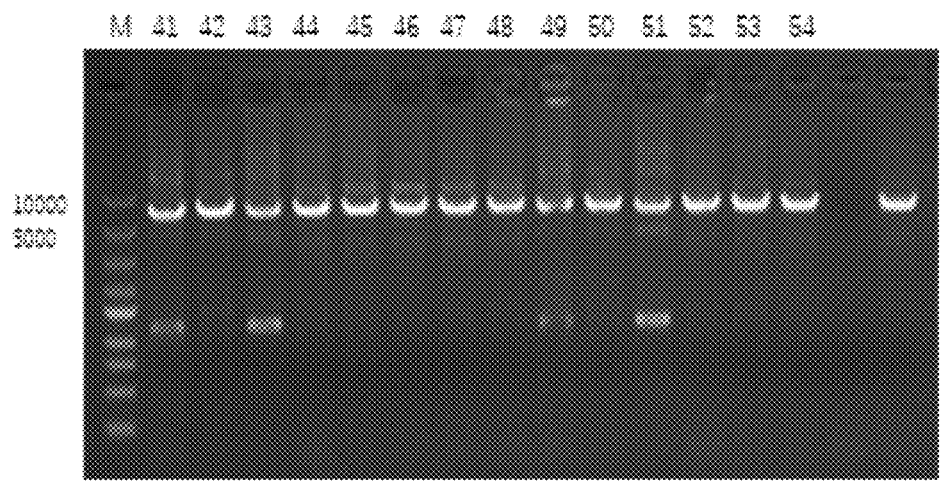
Figure 4:
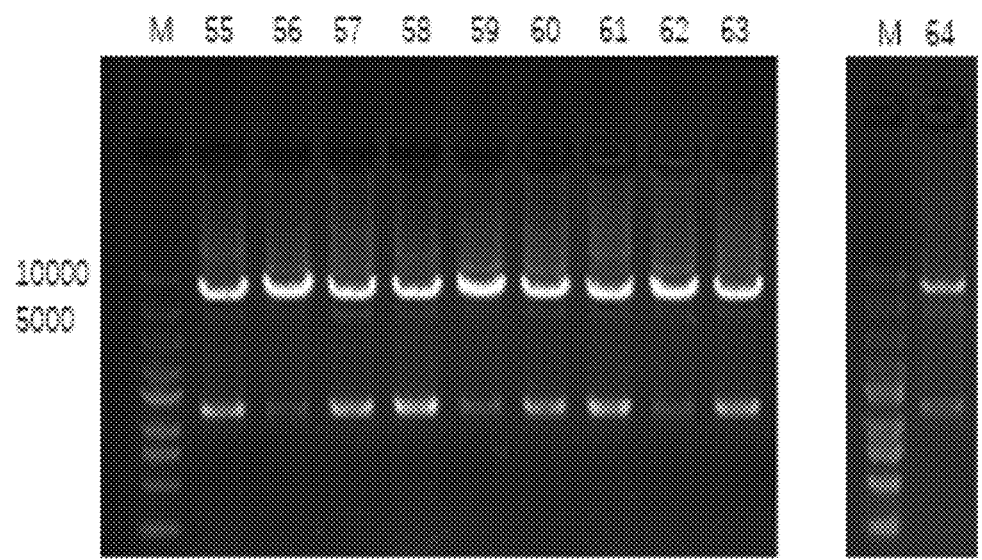
Figure 5:
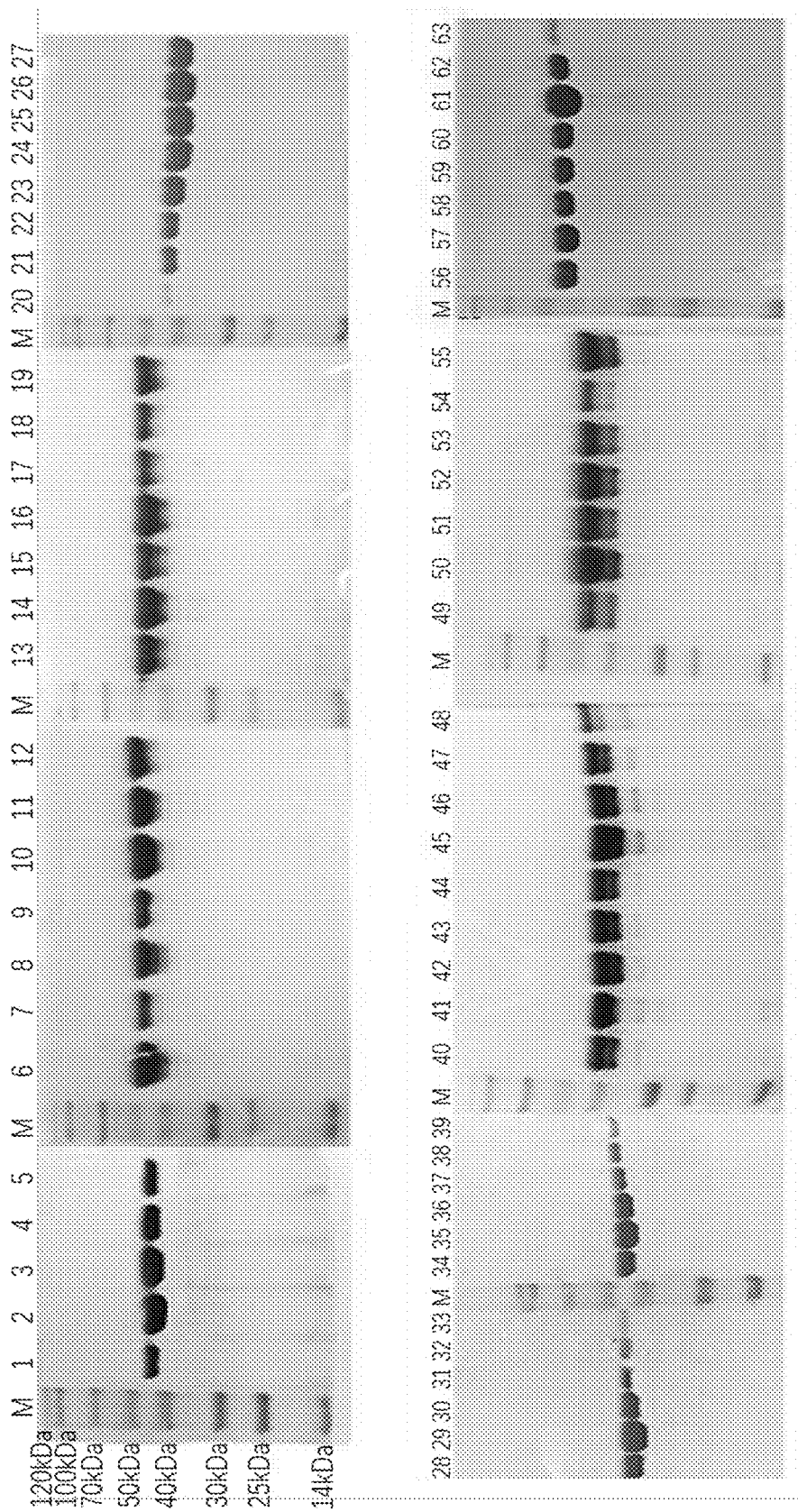

FIG. 5 shows results by SDS-PAGE electrophoresis analysis of expression products obtained from induced fermentation of recombinant E. coli in a shake flask, where M: Maker; and Lanes 1-64: pure enzymes, that are, mutants M1-M64 obtained from induced fermentation of recombinant E. coli BL21/pET28a-KpADH-1 to recombinant E. Coli BL21/pET28a-KpADH-64 in a shake flask.

Figure 6:
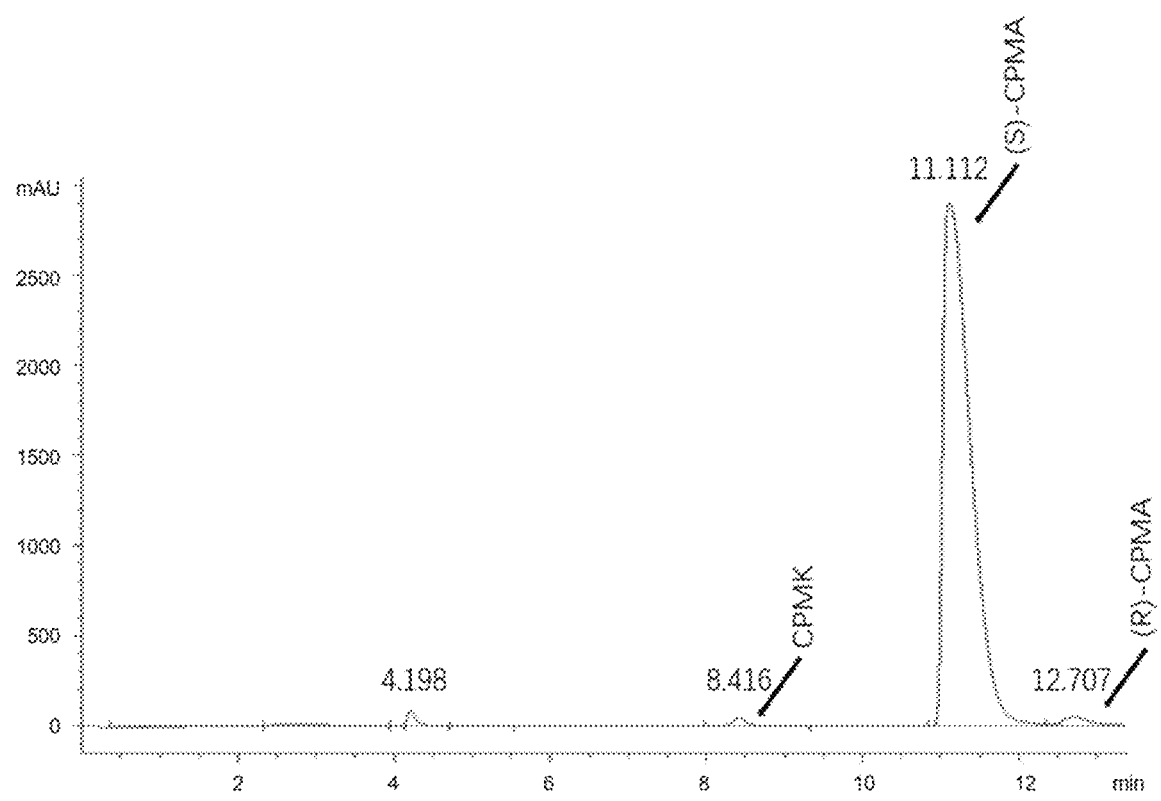

FIG. 6 shows a chiral chromatogram of prochiral diaryl ketone (4-chlorophenyl)-(pyridin-2-yl)-methanone asymmetrically reduced by the mutants M1-M64.

DETAILED DESCRIPTION OF THE PREFERRED EMBODIMENTS

The E. coli BL21(DE3) involved in the following examples is purchased from Beina Biotechnology; the pET-28a(+) plasmid and NADPH involved in the following examples are purchased from Novagen; the glucose dehydrogenase (GDH) and lactate dehydrogenase (LDH) involved in the following examples are purchased from Vazyme Biotech Co., Ltd; D-glucose involved in the following examples is purchased from Generay Biotech. Co., Ltd.; and the prochiral diaryl ketone (4-chlorophenyl)-(pyridin-2-yl)-methanone involved in the following examples is purchased from Sangon Biotech. (Shanghhai) Co., Ltd. (the E. coli BL21(DE3) can be purchased and does not need to be preserved according to the patent procedures).

The media involved in the examples are:

LB liquid medium: yeast powder 5.0 g·L$^{-1}$, tryptone 10.0 g·L$^{-1}$, NaCl 10.0 g·L$^{-1}$, and kanamycin 100 mg·L$^{-1}$.

LB solid medium: yeast powder 5.0 g·L$^{-1}$, tryptone 10.0 g·L$^{-1}$, NaCl 10.0 g·L$^{-1}$, agar powder 15 g/L, and kanamycin 50 mg·L$^{-1}$.

Detection methods involved in examples:

The detection method of enzyme activity of the alcohol dehydrogenase is as follows:

A sodium phosphate buffer (PBS, 100 mM, pH 7.0) containing 1 mM NADPH and 1.0 mM substrate prochiral (4-chlorophenyl)-(pyridin-2-yl)-methanone is stood at 30° C. for 2 min, and then 10 µL of a pure enzyme solution is added to the sodium phosphate buffer, and reacted at 30° C. During the reaction, the change in absorbance of the reaction solution at 340 nm is measured on a microplate reader, and used to calculate the enzyme activity.

The calculation formula of enzyme activity is as follows:

Enzyme activity(U/mL)=$EW \times V \times 10^3/(6220 \times 1)$ where EW is the change in absorbance at 340 nm in 1 min; V is the volume of the reaction solution, in mL; 6220 is the molar extinction coefficient of NADPH, in L/(mol·cm); and 1 is the optical distance, in cm.

Definition of enzyme activity: The amount of enzyme required for catalytic oxidation of 1 µmol NADPH per minute under these conditions is one enzyme activity unit (1 U).

The detection methods of the conversion rate and stereoselectivity in the production of chiral diaryl alcohol (R)-(4-chlorophenyl)-(pyridin-2-yl)-methanol by the asymmetric reduction of prochiral diaryl ketone (4-chlorophenyl)-(pyridin-2-yl)-methanone by alcohol dehydrogenase are as follows:

A sodium phosphate buffer (PBS, 100 mM, pH 7.0) containing 1 mM NADPH and 1.0 mM substrate prochiral (4-chlorophenyl)-(pyridin-2-yl)-methanone is stood at 30° C. for 2 min, and then 10 µL of a pure enzyme solution is added to the sodium phosphate buffer and reacted at 30° C. for 60 min. Then, the reaction is terminated with boiling water. 100 µL of the reaction solution is added to 500 µL of ethyl acetate, shaken for 1-2 min, and centrifuged at 12000 rpm for 2-5 min. The supernatant is added to a centrifuge tube, the organic phase is allowed to evaporate completely, then 500 µL of chromatographic pure ethanol is added, and the conversion rate and e.e. value are analyzed by chiral liquid chromatography.

Chromatographic conditions: Daicel Chiralcel OD-H (5 µm, 250 mm×4.6 mm) liquid chromatographic column, mobile phase n-hexane: ethanol: ethanolamine (90:10:0.01, v/v/v), flow rate 0.8 mL/min, column temperature 30° C., UV detection wavelength 254 nm, injection volume 10 µL, and retention times of (S)-(4-chlorophenyl)-(pyridin-2-yl)-methanol and (R)-(4-chlorophenyl)-(pyridin-2-yl)-methanol 11.12 min and 12.71 min.

The calculation method of conversion rate is as follows:

$$\text{Conversion} = \frac{A_s + A_R}{A_s + A_R + A_{sub}} \times 100\%;$$

The calculation method of ee value is as follows:

$$ee = \frac{A_s - A_R}{A_s + A_R} \times 100\% (S);$$

$$ee = \frac{A_R - A_S}{A_s + A_R} \times 100\% (R);$$

where As: molar concentration of (S)-(4-chlorophenyl)-(pyridin-2-yl)-methanol in the reaction solution; $A_R$: molar concentration of (R)-(4-chlorophenyl)-(pyridin-2-yl)-methanol in the reaction solution; and $A_{sub}$: molar concentration of unreacted (4-chlorophenyl)-(pyridin-2-yl)-methanone in the reaction solution.

Example 1: Production, Expression and Purification of Alcohol Dehydrogenase Mutants A gene encoding the alcohol dehydrogenase having an amino acid sequence as shown in SEQ ID NO: 1 was chemically synthesized (the nucleotide sequence of the gene is as shown in SEQ ID NO: 2, see Table 1 for details). The obtained gene and the pET-28a(+) plasmid were respectively cleaved by Nde I and Xho I and then ligated. The ligation product was transformed into E. coli BL21(DE3), and then the transformed cells were coated on LB solid medium, and incubated at 37° C. for 8-10 h. 5 transformants were picked up from the LB solid medium, inoculated into LB liquid medium, and incubated at 37° C. for 10 hrs. Then the plasmid was extracted, and the extracted plasmid was enzymatically cleaved and sequenced for verification. The plasmid was verified to be correct. That is, a recombinant plasmid pET28a-KpADH comprising the gene encoding wild-type alcohol dehydrogenase and recombinant E. coli BL21/pET28a-KpADH comprising the gene encoding wild-type alcohol dehydrogenase were obtained.

Site-directed mutation was performed by whole plasmid PCR using the obtained recombinant plasmid pET28a-KpADH as a template, to obtain a recombinant plasmid comprising a gene encoding the alcohol dehydrogenase mutant K36I (mutation of lysine at position 36 to isoleucine), T132D (mutation of threonine at position 132 to aspartate), N159D (mutation of asparagine at position 159 to aspartate), K210E (mutation of lysine at position 210 to glutamate), T248A (mutation of threonine at position 248 to alanine), Q272L (mutation of glutamine at position 272 to leucine), K36I/T132D, K36I/N159D, K26I/K210E, K26I/T248A, K26I/Q272L, T132D/N159D, T132D/K210E, T132D/T248A, T132D/Q272L, N159D/K210E, N159D/T248A, N159D/Q272L, K210E/T248A, K210E/Q272L, T248A/Q272L, K36I/T132D/N159D, K36I/T132D/K210E, K36I/T132D/T248A, K36I/T132D/Q272L, K36I/N159D/K210E, K36I/N159D/T248A, K36I/N159D/Q272L, K36I/K219E/T248A, K36I/K210E/Q272L, K36I/T248A/Q272L, T132D/N159D/K210E, T132D/N159D/T248A, T132D/N159D/Q272L, T132D/K210E/T248A, T132D/K210E/Q272L, T132D/T248A/Q272L, N159D/K210E/T248A, N159D/K210E/Q272L, N159D/K248A/Q272L, K210E/T248A/Q272L, K36I/T132D/N159D/K210E, K36I/T132D/N159D/T248A, K36I/T132D/N159D/Q272L, K36I/T132D/K210E/T248A, K36I/T132D/K210E/Q272L, K36I/T132D/T248A/Q272L, K36I/N159D/K210E/T248A, K36I/N159D/K210E/Q272L, K36I/N159D/T248A/Q272L, K36I/K210E/T248A/Q272L, T132D/N159D/K210E/Q272L, T132D/N159D/T248A/Q272L, T132D/K210E/T248A/Q272L, T132D/N159D/K210E/T248A, N159D/K210E/T248A/Q272L, K36I/T132D/N159D/K210E/T248A, K36I/T132D/N159D/K210E/Q272L, K36I/T132D/N159D/T248A/Q272L, K36I/T132D/K210E/T248A/Q272L, K36I/N159D/K210E/T248A/Q272L, T132D/N159D/K210E/T248A/Q272L, K36I/T132D/N159D/K210E/T248A/Q272L, K36I/T132D/N159D/K210E/T248A/Q272L/Q136N/F161V/S196G/E214G/S237C, or Q136N/F161V/S196G/E214G/S237C (mutation of glutamine at position 136 to asparagine, mutation of phenylalanine at position 161 to valine, mutation of serine at position 196 to glycine, mutation of glutamate at position 214 to glycine, and mutation of serine at position 237 to cysteine) respectively. The alcohol dehydrogenase mutants were respectively designated as M1-M64 and S5.

The primers for mutations K36I, T132D, N159D, K210E, T248A, Q272L, Q136N, F161V, S196G, E214G, and S237C are:

```
K36I-F:
                               (SEQ ID NO: 3)
AGAAGTCAAGACattGCTGAT;

K36I-R:
                               (SEQ ID NO: 4)
TAACTTATCAGCaatGTCTTG;

T132D-F:
                               (SEQ ID NO: 5)
GCTTCAATTATGgatCCACATAGA;

T132D-R:
                               (SEQ ID NO: 6)
TTGTCTATGTGGatcCATAATTGA;

N159D-F:
                               (SEQ ID NO: 7)
AATGCTTATGAAgatGTCGTT;

N159D-R:
                               (SEQ ID NO: 8)
AGCAGTAACGAcatCTTCATA;

K210E-F:
                               (SEQ ID NO: 9)
GAAGACGTCACTgaaAAACTAAAT;

K210E-R:
                               (SEQ ID NO: 10)
TTCATTTAGTTTttcAGTGACGTC;

T248A-F:
                               (SEQ ID NO: 11)
GATGTCGCCAAAgcaCACGTTTTG;

T248A-R:
                               (SEQ ID NO: 12)
ACCCAAAACGTGtgcTTTGGCGAC;

Q272L-F:
                               (SEQ ID NO: 13)
GGCGCCTTCTCTctgCAAGATATT;

Q272L-R:
                               (SEQ ID NO: 14)
AACAATATCTTGcagAGAGAAGGC;

Q136N-F:
                               (SEQ ID NO: 15)
CCACATAGAaatAATGATCCA;

Q136N-R:
                               (SEQ ID NO: 16)
TGGATCATTATTTCTATGTGG;

F161V-F:
                               (SEQ ID NO: 17)
TATGAAAATGTCgttACTGCT;

F161V-R:
                               (SEQ ID NO: 18)
ACAATAAGCAGTAACGACATT;

S196G-F:
                               (SEQ ID NO: 19)
ACTATCCACCCAggtTTCGTT;

S196G-R:
                               (SEQ ID NO: 20)
TCCGAAAACGAAACCTGGGTG;

E214G-F:
                               (SEQ ID NO: 21)
CTAAATggtACTTGTGAAATT;

E214G-R:
                               (SEQ ID NO: 22)
AATTTCACAAGTACCATTTAG;

S237C-F:
                               (SEQ ID NO: 23)
AAGACTCACTTCtgtCAATTC;

S237C-R:
                               (SEQ ID NO: 24)
ATCAATGAATTGACAGAAGTG,
```

PCR reaction system (50 μL): KOD enzyme (2.5 U/mL) 1.0 μL, template (5-50 ng) 1.0 μL, dNTP 4.0 μL, 10× reaction buffer 5.0 μL, upstream and downstream primers each 1.0 μL, and ddH$_2$O q.s. to 50 μL.

Conditions for PCR amplification of products: (1) denaturation at 94° C. for 3 min, 10-15 cycles of (2) denaturation at 94° C. for 30 sec, (3) annealing at 54° C. for 30 sec, and (4) extension at 72° C. for 150 sec, and final extension at 72° C. for 10 min. The PCR product was stored at 4° C.

The product after PCR amplification was detected by 1% agarose gel electrophoresis. After the detection, 0.5 μL of a methylation template digestive enzyme (Dpn I) was added to 10 μL of the amplified product, and mixed uniformly by blowing and aspirating with a pipette tip. After reaction for 1 hr at 37° C., the amplified product after treatment with Dpn I was transformed into *E. coli* BL21(DE3), and then the transformed cells were coated on LB solid medium, and incubated at 37° C. for 8-10 h. 5 transformants were picked up from the LB solid medium, inoculated into LB liquid medium, and incubated at 37° C. for 10 h. Then the plasmid was extracted, and the extracted plasmid was enzymatically cleaved (the verification results are shown in FIGS. 1-4) and sequenced for verification. The plasmid was verified to be correct. That is, recombinant plasmid pET28a-KpADH-1 to recombinant plasmid pET28a-KpADH-65 comprising respectively the genes encoding alcohol dehydrogenase mutants M1-M64 and S5 and recombinant E. coli BL21/pET28a-KpADH-1 to recombinant E. coli BL21/pET28a-KpADH-65 comprising respectively the genes encoding alcohol dehydrogenase mutants M1-M64 and S5 were obtained.

The obtained recombinant E. coli BL21/pET28a-KpADH and recombinant E. coli BL21/pET28a-KpADH-1 to recombinant E. coli BL21/pET28a-KpADH-65 were respectively coated on LB solid medium, and incubated at 37° C. for 8-10 h, to obtain single colonies. A single colony was picked up and inoculated into LB liquid medium, and incubated at 37° C. for 12-14 h to obtain a seed suspension. The seed suspension was inoculated into LB liquid medium in an amount of 2% (v/v), and incubated at 37° C. and 200 rpm until $OD_{600}$ reached 0.8. IPTG was added to at a final concentration of 0.2 mM, and the induction culture was continued for 8 h at 25° C. to obtain a fermentation broth. The fermentation broth was centrifuged at 4° C. and 8000 rpm for 10 min, and the cells were collected. The collected cells were suspended in potassium phosphate buffer (100 mmol·$L^{-1}$, pH 6.0) and ultrasonically homogenized. A cell homogenate supernatant containing respectively wild-type alcohol dehydrogenase, alcohol dehydrogenase mutants M1-M64 or alcohol dehydrogenase mutant S5 was collected.

The obtained cell homogenate supernatant was purified by running through an affinity column HisTrap FF crude (nickel column). The purification process was as follows. The nickel column was equilibrated with buffer A (20 mmol·$L^{-1}$ sodium phosphate, 500 mmol·$L^{-1}$ NaCl, 20 mmol·$L^{-1}$ imidazole, pH 7.4), and the cell homogenate supernatant obtained in Example 1 was allowed to run through the nickel column. The proteins that were not bound to the nickel column were eluted off using buffer A. After the flow-through peak ran out, elution with a gradient from buffer A to buffer B (20 mmol·$L^{-1}$ sodium phosphate, 500 mmol·$L^{-1}$ NaCl, 500 mmol·$L^{-1}$ imidazole, pH 7.4) was carried out, to elute off the recombinant protein binding to the nickel column. In this way, a pure enzyme solution of wild-type alcohol dehydrogenase, alcohol dehydrogenase mutants M1-M64, or alcohol dehydrogenase mutant S5 was obtained.

The obtained pure enzyme solution of alcohol dehydrogenase mutants M1-M64 or alcohol dehydrogenase mutant S5 was analyzed by SDS-PAGE. The analysis results are shown in FIG. 5.

It can be seen from FIG. 5 that the pure enzyme solution of alcohol dehydrogenase mutants M1-M64 or alcohol dehydrogenase mutant S5 shows a single band at about 45 kDa, and contains less protein impurities, indicating that the purification effect of the nickel column is good.

Example 2: Thermal Stability of Alcohol Dehydrogenase Mutants

The pure enzyme solution of wild-type alcohol dehydrogenase, alcohol dehydrogenase mutants M1-M64 or alcohol dehydrogenase mutant S5 obtained in Example 1 was allowed to stand for 15 min in a water bath at a temperature of 40-60° C. respectively. After 15 min, the enzyme activity of the wild-type alcohol dehydrogenase, alcohol dehydrogenase mutants M1-M64 and alcohol dehydrogenase mutant S5 was determined. The relative activity was calculated by the percentages of the remaining activity after standing in the water bath relative to the activity before standing in the water bath at different temperatures taken as 100%, to determine the $T_{50}^{15}$ values of the wild-type alcohol dehydrogenase, alcohol dehydrogenase mutants M1-M64 and alcohol dehydrogenase mutant S5 (where $T_{50}^{15}$ is the temperature at which the activity of the alcohol dehydrogenase after standing 15 min in the water bath is half of the activity before standing in the water bath. The test results are shown in Table 2).

The pure enzyme solution of wild-type alcohol dehydrogenase, alcohol dehydrogenase mutants M1-M64 or alcohol dehydrogenase mutant S5 obtained in Example 1 was allowed to stand in a water bath at a temperature of 30-45° C. respectively. A sample was taken periodically to determine the activity of wide-type alcohol dehydrogenase, alcohol dehydrogenase mutants M1-M64 and alcohol dehydrogenase mutant S5. The relative activity was calculated by the percentages of the remaining activity after standing in the water bath relative to the activity before standing in the water bath at different temperatures taken as 100%, to determine the half-life $t_{1/2}$ of wide-type alcohol dehydrogenase, alcohol dehydrogenase mutants M1-M64 and alcohol dehydrogenase mutant S5 (where the half-life $t_{1/2}$ is the time over which the activity is halved upon standing at a certain temperature). A fitted inactivation curve was plotted from the half-life of wide-type alcohol dehydrogenase, alcohol dehydrogenase mutants M1-M64 and alcohol dehydrogenase mutant S5 at different temperatures according to the Arrhennius equation, and the deactivation activation energy $E_d$ of wide-type alcohol dehydrogenase, alcohol dehydrogenase mutants M1-M64 and alcohol dehydrogenase mutant S5 was calculated (the calculation results as shown in Table 2).

The calculation formula of deactivation activation energy is as follows:

$$E_d = -RT(lnk - lnA);$$

$$k = \frac{ln2}{t_{1,2}};$$

where R: molar gas constant; T: corresponding temperature; k: deactivation rate, $t_{1/2}$: half-life at corresponding temperature, and A: pre-exponential factor.

It can be seen from Table 2 that the thermal stability of alcohol dehydrogenase mutants M1-M64 is significantly improved compared with the wild-type alcohol dehydrogenase. Among them, the alcohol dehydrogenase mutant M63 has the most excellent thermal stability, has a $T_{50}^{15}$ and an $E_d$ reaching 53.1° C. and 989.13 kJ/mol respectively, which are 11.1° C. and 32.06 kJ/mol higher than the wild type; and has a half-life $t_{1/2}$ at 45° C. that is 3000 times that of the wild-type alcohol dehydrogenase. The thermal stability of alcohol dehydrogenase mutant S5 decreases obviously compared with the wild-type alcohol dehydrogenase.

TABLE 2

T$_{50}^{15}$, E$_d$, and t$_{1/2}$ at 45° C. of wild-type alcohol dehydrogenase, alcohol dehydrogenase mutants M1-M64 and alcohol dehydrogenase mutant S5

| No. | T$_{50}^{15}$ ° C. | Ed kJ/mol | t$_{1/2}$ min |
|---|---|---|---|
| Wild type | 42 ± 0.1 | 957.07 | 1.1 |
| M1 | 43.5 ± 0.2 | 959.95 | nd |
| M2 | 44.7 ± 0.2 | 965.39 | nd |
| M3 | 43.9 ± 0.1 | 960.71 | nd |
| M4 | 43.8 ± 0.2 | 960.56 | nd |
| M5 | 45.8 ± 0.3 | 968.26 | nd |
| M6 | 43.6 ± 0.2 | 960.10 | nd |
| M7 | 45.6 ± 0.1 | 966.78 | nd |
| M8 | 44 ± 0.3 | 962.23 | nd |
| M9 | 45.2 ± 0.2 | 965.57 | nd |
| M10 | 46.8 ± 0.3 | 970.42 | nd |
| M11 | 44.5 ± 0.2 | 963.45 | nd |
| M12 | 44.6 ± 0.2 | 963.90 | nd |
| M13 | 46.6 ± 0.3 | 970.06 | nd |
| M14 | 47.5 ± 0.1 | 972.79 | nd |
| M15 | 45.8 ± 0.2 | 967.99 | nd |
| M16 | 44.4 ± 0.1 | 963.29 | nd |
| M17 | 45.8 ± 0.2 | 967.84 | nd |
| M18 | 44 ± 0.3 | 962.23 | nd |
| M19 | 47 ± 0.2 | 971.27 | nd |
| M20 | 45.5 ± 0.2 | 966.78 | nd |
| M21 | 47 ± 0.3 | 971.27 | nd |
| M22 | 45.8 ± 0.2 | 967.39 | nd |
| M23 | 47.6 ± 0.4 | 972.54 | nd |
| M24 | 49.1 ± 0.3 | 977.65 | nd |
| M25 | 46.9 ± 0.1 | 970.72 | nd |
| M26 | 45.7 ± 0.1 | 967.23 | nd |
| M27 | 46.9 ± 0.3 | 970.72 | nd |
| M28 | 45.2 ± 0.3 | 965.87 | nd |
| M29 | 48.5 ± 0.2 | 975.83 | nd |
| M30 | 46.6 ± 0.2 | 969.66 | nd |
| M31 | 48.5 ± 0.3 | 975.83 | nd |
| M32 | 46.4 ± 0.4 | 969.36 | nd |
| M33 | 48 ± 0.3 | 973.45 | nd |
| M34 | 46.4 ± 0.2 | 968.60 | nd |
| M35 | 49 ± 0.1 | 977.34 | nd |
| M36 | 47.8 ± 0.1 | 973.30 | nd |
| M37 | 49 ± 0.3 | 977.34 | nd |
| M38 | 47.9 ± 0.3 | 973.15 | nd |
| M39 | 46.7 ± 0.2 | 966.48 | nd |
| M40 | 47.5 ± 0.3 | 971.93 | nd |
| M41 | 49.1 ± 0.1 | 976.63 | nd |
| M42 | 48.2 ± 0.2 | 974.05 | nd |
| M43 | 49.1 ± 0.3 | 976.78 | nd |
| M44 | 47.4 ± 0.4 | 971.63 | nd |
| M45 | 51.1 ± 0.2 | 983.7 | nd |
| M46 | 48.9 ± 0.2 | 976.48 | nd |
| M47 | 50.6 ± 0.1 | 981.33 | nd |
| M48 | 49.2 ± 0.2 | 977.39 | nd |
| M49 | 46.4 ± 0.1 | 968.90 | nd |
| M50 | 48.8 ± 0.1 | 976.02 | nd |
| M51 | 50.3 ± 0.3 | 980.87 | nd |
| M52 | 49.7 ± 0.3 | 979.21 | nd |
| M53 | 47.8 ± 0.1 | 976.32 | nd |
| M54 | 49.3 ± 0.4 | 978.26 | nd |
| M55 | 50.9 ± 0.2 | 983.11 | nd |
| M56 | 48.9 ± 0.2 | 976.48 | nd |
| M57 | 51.3 ± 0.3 | 984.33 | nd |
| M58 | 48.7 ± 0.1 | 976.43 | nd |
| M59 | 50.7 ± 0.3 | 982.50 | nd |
| M60 | 52.4 ± 0.6 | 986.93 | nd |
| M61 | 50.5 ± 0.2 | 981.63 | nd |
| M62 | 51.3 ± 0.1 | 984.21 | nd |
| M63 | 53.1 ± 0.4 | 989.13 | 3000 |
| M64 | 51.5 ± 0.1 | 984.14 | 2400 |
| S5 | 41 ± 0.4 | 953.10 | 0.9 | nd: not detected.

Example 3: Kinetic Parameters and Stereoselectivity in the Production of Chiral Diaryl Alcohol (4-Chlorophenyl)-(Pyridin-2-Yl)-Methanol by the Asymmetric Reduction of Prochiral Diaryl Ketone (4-Chlorophenyl)-(Pyridin-2-Yl)-Methanone by Alcohol Dehydrogenase Mutants The initial reduction activity of wild-type alcohol dehydrogenase and alcohol dehydrogenase mutants M63, M64 and S5 obtained in Example 1 were respectively determined with 0.1-5 mM prochiral diaryl ketone (4-chlorophenyl)-(pyridin-2-yl)-methanone as a substrate. The data was fitted by the nonlinear regression method in Graph Pad Prism 7.0 software, to obtain the $K_m$ and $V_{max}$ in Michaelis-Menten equation. Then $k_{cat}$ and $k_{cat}/K_m$ were calculated. The calculation results are shown in Table 3.

$k_{cat}$ is calculated by the formula $k_{cat}=V_{max} \cdot M/60$, where M is the molecular weight of the enzyme, in kDa.

It can be known from Table 3 that the catalytic efficiency of alcohol dehydrogenase mutant M63 in the asymmetric reduction of prochiral diaryl ketone (4-chlorophenyl)-(pyridin-2-yl)-methanone to produce (R)-(4-chlorophenyl)-(pyridin-2-yl)-methanol is obviously improved compared with the wild-type alcohol dehydrogenase, and is 1.3 times that of the wild-type alcohol dehydrogenase. The catalytic efficiency of alcohol dehydrogenase mutant M64 in the asymmetric reduction of prochiral diaryl ketone (4-chlorophenyl)-(pyridin-2-yl)-methanone to produce (S)-(4-chlorophenyl)-(pyridin-2-yl)-methanol is close to that of the wild type, but is 1.35 times that of the alcohol dehydrogenase mutant S5. The catalytic efficiency of alcohol dehydrogenase mutant S5 in the asymmetric reduction of prochiral diaryl ketone (4-chlorophenyl)-(pyridin-2-yl)-methanone to produce (S)-(4-chlorophenyl)-(pyridin-2-yl)-methanol is decreased compared with the wild type.

The stereoselectivity of wild-type alcohol dehydrogenase and alcohol dehydrogenase mutants M63, M64 and S5 obtained in Example 1 in the asymmetric reduction of prochiral diaryl ketone (4-chlorophenyl)-(pyridin-2-yl)-methanone to produce chiral diaryl alcohol (4-chlorophenyl)-(pyridin-2-yl)-methanol was detected. The detection results are shown in Table 3.

It can be known from Table 3 that the stereoselectivity of alcohol dehydrogenase mutants M63, M64 and S5 in the asymmetric reduction of prochiral diaryl ketone (4-chlorophenyl)-(pyridin-2-yl)-methanone to produce chiral diaryl alcohol (4-chlorophenyl)-(pyridin-2-yl)-methanol is not decreased compared with the wild-type alcohol dehydrogenase. Moreover, it can be known from Table 3 that the wild-type alcohol dehydrogenase can asymmetrically reduce the prochiral diaryl ketone (4-chlorophenyl)-(pyridin-2-yl)-methanone to produce (R)-(4-chlorophenyl)-(pyridin-2-yl)-methanol, with an e.e. of 87.1% (R). Compared with the wild-type alcohol dehydrogenase, the alcohol dehydrogenase mutant M64 has reversed stereoselectivity in the asymmetric reduction of prochiral diaryl ketone (4-chlorophenyl)-(pyridin-2-yl)-methanone to produce chiral diaryl alcohol (4-chlorophenyl)-(pyridin-2-yl)-methanol, and can asymmetrically reduce the prochiral diaryl ketone (4-chlorophenyl)-(pyridin-2-yl)-methanone to produce (S)-(4-chlorophenyl)-(pyridin-2-yl)-methanol, with an e.e. value of up to 97.3% (S).

TABLE 3

Kinetic parameters and stereoselectivity in the production of chiral diaryl alcohol
(4-chlorophenyl)-(pyridin-2-yl)-methanol by the asymmetric reduction of prochiral
diaryl ketone (4-chlorophenyl)-(pyridin-2-yl)-methanone by the wild-type alcohol
dehydrogenase and alcohol dehydrogenase mutants M63, M64 and S5

| No. | $K_m$ (mM) | $V_{max}$ ($\mu mol \cdot min^{-1} \cdot mg^{-1}$) | $k_{cat}$ ($s^{-1}$) | $k_{cat}/K_m$ ($s^{-1} \cdot mM^{-1}$) | e.e. (%) |
|---|---|---|---|---|---|
| Wild type | 0.95 ± 0.1 | 31.75 ± 1.4 | 20.09 ± 1.0 | 21.15 | 87.1 (R) |
| S5 | 1.09 ± 0.1 | 24.44 ± 2.6 | 16.09 ± 1.7 | 14.76 | 97.3 (S) |
| M63 | 0.83 ± 0.2 | 32.83 ± 3 | 22.8 ± 2.14 | 27.47 | 87.2 (R) |
| M64 | 0.86 ± 0.14 | 25.12 ± 1.6 | 17.44 ± 1.1 | 20.27 | 97.2 (S) |

Example 4. Conversion Efficiency in the Production of (S)-(4-Chlorophenyl)-(Pyridin-2-Yl)-Methanol by the Asymmetric Reduction of Prochiral Diaryl Ketone (4-Chlorophenyl)-(Pyridin-2-Yl)-Methanone by Alcohol Dehydrogenase Mutant The wild-type alcohol dehydrogenase and alcohol dehydrogenase mutant M64 obtained in Example 1 were added in an amount of 7 g/L respectively to 100 mM potassium phosphate buffer (pH 7.0) containing 100 mM, 200 mM, or 500 mM prochiral diaryl ketone(4-chlorophenyl)-(pyridin-2-yl)-methanone, reacted at 30° C., pH 7.0, and 200 rpm for 12 h to obtain a reaction solution. In addition to the prochiral diaryl ketone (4-chlorophenyl)-(pyridin-2-yl)-methanone, the potassium phosphate buffer further contained 0.02 mM coenzyme NADP$^+$, 1.5 mM glucose, 1.5 mM glucose dehydrogenase GDH and 5% (v/v) ethanol.

The conversion rates in the asymmetric reduction of prochiral diaryl ketone (4-chlorophenyl)-(pyridin-2-yl)-methanone to produce (S)-(4-chlorophenyl)-(pyridin-2-yl)-methanol by the wild-type alcohol dehydrogenase and alcohol dehydrogenase mutant M64 at different reaction times were detected, and the conversion efficiency (that is, space time yield) in the asymmetric reduction of prochiral diaryl ketone (4-chlorophenyl)-(pyridin-2-yl)-methanone to produce (S)-(4-chlorophenyl)-(pyridin-2-yl)-methanol by the wild-type alcohol dehydrogenase and alcohol dehydrogenase mutant M64 was calculated. The detection results were shown in Tables 4-5.

It can be known from Tables 4-5 that in case of 100 mM substrate, the wild-type alcohol dehydrogenase and alcohol dehydrogenase mutant M64 achieve a conversion rate of >99.9% respectively at 4 h and 2 h of reaction. Therefore, compared with the wild-type alcohol dehydrogenase, the alcohol dehydrogenase mutant M64 enables an obviously improved conversion efficiency in the asymmetric reduction of prochiral diaryl ketone (4-chlorophenyl)-(pyridin-2-yl)-methanone to produce (S)-(4-chlorophenyl)-(pyridin-2-yl)-methanol. Also, it can be known from Tables 4-5 that when 500 mM prochiral diaryl ketone (4-chlorophenyl)-(pyridin-2-yl)-methanone is added, the wild-type alcohol dehydrogenase fails to convert it completely, but the conversion efficiency enabled by the alcohol dehydrogenase mutant M64 is not affected by high concentration of prochiral diaryl ketone (4-chlorophenyl)-(pyridin-2-yl)-methanone. It can be seen that the alcohol dehydrogenase mutant M64 is adapted to an environment with a high concentration of prochiral diaryl ketone (4-chlorophenyl)-(pyridin-2-yl)-methanone, and can asymmetrically reduce the high concentration of prochiral diaryl ketone (4-chlorophenyl)-(pyridin-2-yl)-methanone to produce (S)-(4-chlorophenyl)-(pyridin-2-yl)-methanol with a high conversion efficiency (that is, space time yield) that is up to 651 g/(L·d).

TABLE 4

Conversion rate in the production of (S)-(4-chlorophenyl)-(pyridin-2-yl)-methanol by the asymmetric reduction of prochiral diaryl ketone (4-chlorophenyl)-(pyridin-2-yl)-methanone by the wide-type alcohol dehydrogenase

| Reaction time (h) | Conversion rate (%) | | |
|---|---|---|---|
| | 100 mM | 200 mM | 500 mM |
| 0.5 | 60.5 | 35.6 | 19.7 |
| 1 | 95.5 | 56.9 | 24.1 |
| 2 | 97.5 | 82.0 | 26.2 |
| 3 | 99.8 | 95.5 | 27.6 |
| 4 | >99.9 | 98.6 | 28 |
| 6 | >99.9 | >99.9 | 28.1 |
| 8 | >99.9 | >99.9 | 28.1 |
| 12 | >99.9 | >99.9 | 28.2 |

TABLE 5

Conversion rate in the production of (S)-(4-chlorophenyl)-(pyridin-2-yl)-methanol by the asymmetric reduction of prochiral diaryl ketone (4-chlorophenyl)-(pyridin-2-yl)-methanone by the alcohol dehydrogenase mutant M64

| Reaction time (h) | Conversion rate (%) | | |
|---|---|---|---|
| | 100 mM | 200 mM | 500 mM |
| 0.5 | 95 | 81.3 | 43 |
| 1 | 98.3 | 95.2 | 58.6 |
| 2 | >99.9 | 98.9 | 86.2 |
| 3 | >99.9 | >99.9 | 98.3 |
| 4 | >99.9 | >99.9 | 99.3 |
| 6 | >99.9 | >99.9 | >99.9 |
| 8 | >99.9 | >99.9 | >99.9 |
| 12 | >99.9 | >99.9 | >99.9 |

While the present invention has been described above by way of preferred examples, the present invention is not limited thereto. Various modifications and changes can be made by those skilled in the art without departing from the spirit and scope of the present invention as defined by the appended claims.

What is claimed is:

1. An alcohol dehydrogenase mutant, wherein the mutant is obtained by mutating lysine at position 36, threonine at position 132, asparagine at position 159, lysine at position 210, threonine at position 248 and/or glutamine at position 272 in the starting amino acid sequence as shown in SEQ ID NO: 1 of alcohol dehydrogenase; or mutating lysine at position 36, threonine at position 132, asparagine at position 159, lysine at position 210, threonine at position 248, glutamine at position 272, glutamine at position 136, phenylalanine at position 161, serine at position 196, glutamate at position 214 and serine at position 237 in the starting amino acid sequence as shown in SEQ ID NO: 1 of alcohol dehydrogenase.

2. The alcohol dehydrogenase mutant according to claim 1, wherein the mutant is obtained by mutating lysine at position 36 to isoleucine, threonine at position 132 to aspartate, asparagine at position 159 to aspartate, lysine at position 210 to glutamate, threonine at position 248 to alanine and/or glutamine at position 272 to leucine; or mutating lysine at position 36 to isoleucine, threonine at position 132 to aspartate, asparagine at position 159 to aspartate, lysine at position 210 to glutamate, threonine at position 248 to alanine, glutamine at position 272 to leucine, glutamine at position 136 to asparagine, phenylalanine at position 161 to valine, serine at position 196 to glycine, glutamate at position 214 to glycine, and serine at position 237 to cysteine.

3. A gene encoding the alcohol dehydrogenase mutant according to claim 1.

4. A recombinant plasmid comprising the gene according to claim 3.

5. The recombinant plasmid according to claim 4, wherein the vector of the recombinant plasmid is pET-28a(+) plasmid, pET-28b(+) plasmid or pET-20b(+) plasmid.

6. A host cell comprising the gene according to claim 3.

7. A method for producing the alcohol dehydrogenase mutant according to claim 1, comprising steps of:
inoculating a host cell comprising a gene encoding the alcohol dehydrogenase mutant into a fermentation medium for fermentation to obtain a fermentation broth;
centrifuging the fermentation broth to collect the bacterial cells;
homogenizing the bacterial cells and centrifuging to obtain a cell homogenate supernatant; and
purifying the alcohol dehydrogenases from the cell homogenate supernatant.

8. A method for producing a chiral diaryl alcohol, comprising adding the alcohol dehydrogenase mutant according to claim 1 to a reaction system comprising a prochiral diaryl ketone for reaction; and extracting the resulting reaction solution to obtain a chiral diaryl alcohol.

9. The method for producing a chiral diaryl alcohol according to claim 8, wherein the reaction system further comprises a coenzyme, and a coenzyme regeneration system comprising D-glucose and a glucose dehydrogenase, or a phosphite and a phosphite dehydrogenase, or a formate and a formate dehydrogenase, or a lactate and a lactate dehydrogenase, or glycerol and a glycerol dehydrogenase.

* * * * *

SEQUENCE LISTING

<160> NUMBER OF SEQ ID NOS: 24

<210> SEQ ID NO 1
<211> LENGTH: 342
<212> TYPE: PRT
<213> ORGANISM: Artificial Sequence
<220> FEATURE:
<223> OTHER INFORMATION: Alcohol Dehydrogenase

<400> SEQUENCE: 1

Met Ser Val Leu Ile Ser Gly Ala Ser Gly Tyr Ile Ala Lys His Ile
1               5                   10                  15

Val Arg Val Leu Leu Glu Gln Asn Tyr Lys Val Ile Gly Thr Val Arg
            20                  25                  30

Ser Gln Asp Lys Ala Asp Lys Leu Leu Lys Gln Tyr Asn Asn Pro Asn
        35                  40                  45

Leu Ser Tyr Glu Ile Val Pro Glu Ile Ala Asn Leu Asp Ala Phe Asp
    50                  55                  60

Asp Ile Phe Lys Lys His Gly Lys Glu Ile Lys Tyr Val Ile His Ala
65                  70                  75                  80

Ala Ser Pro Val Asn Phe Gly Ala Lys Asp Leu Glu Lys Asp Leu Val
                85                  90                  95

Ile Pro Ala Ile Asn Gly Thr Lys Asn Met Phe Glu Ala Ile Lys Lys
            100                 105                 110

Tyr Ala Pro Asp Thr Val Glu Arg Val Val Met Thr Ala Ser Tyr Ala
        115                 120                 125

Ser Ile Met Thr Pro His Arg Gln Asn Asp Pro Thr Leu Thr Leu Asp
    130                 135                 140

Glu Glu Thr Trp Asn Pro Val Thr Glu Glu Asn Ala Tyr Glu Asn Val
145                 150                 155                 160

Phe Thr Ala Tyr Cys Ala Ser Lys Thr Phe Ala Glu Lys Glu Ala Trp
                165                 170                 175

Lys Phe Val Lys Glu Asn Ser Asp Ala Val Lys Phe Lys Leu Thr Thr
            180                 185                 190

Ile His Pro Ser Phe Val Phe Gly Pro Gln Asn Phe Asp Glu Asp Val
        195                 200                 205

Thr Lys Lys Leu Asn Glu Thr Cys Glu Ile Ile Asn Gly Leu Leu His
    210                 215                 220

Ala Pro Phe Asp Thr Lys Val Glu Lys Thr His Phe Ser Gln Phe Ile
225                 230                 235                 240

Asp Val Arg Asp Val Ala Lys Thr His Val Leu Gly Phe Gln Lys Asp
                245                 250                 255

Glu Leu Ile Asn Gln Arg Leu Leu Leu Cys Asn Gly Ala Phe Ser Gln
            260                 265                 270

Gln Asp Ile Val Asn Val Phe Asn Glu Asp Phe Pro Glu Leu Lys Gly
        275                 280                 285

Gln Phe Pro Pro Glu Asp Lys Asp Thr Asp Leu Asn Lys Gly Val Thr
    290                 295                 300

Gly Cys Lys Ile Asp Asn Glu Lys Thr Lys Lys Leu Leu Ala Phe Glu
305                 310                 315                 320

Phe Thr Pro Phe His Lys Thr Ile His Asp Thr Val Tyr Gln Ile Leu
                325                 330                 335

His Lys Glu Gly Arg Val
            340

-continued

```
<210> SEQ ID NO 2
<211> LENGTH: 1029
<212> TYPE: DNA
<213> ORGANISM: Artificial Sequence
<220> FEATURE:
<223> OTHER INFORMATION: Alcohol Dehydrogenase

<400> SEQUENCE: 2
atgagcgtat taattagtgg tgcttctgga tacattgcca acatatcgt cagagttctt      60 ttggaacaaa attacaaagt aattggtact gttagaagtc aagacaaagc tgataagtta     120
ttgaaacaat ataataatcc taatttgtct tatgaaattg tacctgaaat agcaaactta     180
gatgcttttg atgacatttt taagaaacat ggtaaggaaa taaatatgt cattcatgca     240 gcttcaccag tgaacttcgg cgcaaaagat ttggaaaaag atttagttat tcctgccatt     300
aatggtacca agaatatgtt cgaagctatt aaaaagtatg ccccagatac tgtcgaacgt     360
gttgtaatga ctgcttctta tgcttcaatt atgaccccac atagacaaaa tgatccaact     420
ttaactttag atgaagaaac ttggaatcca gtaactgaag aaaatgctta tgaaaatgtc     480
ttcactgctt attgtgcttc aaaaactttt gctgaaaagg aagcttggaa gttcgttaaa     540
gaaaatagtg atgctgttaa gtttaaacta accactatcc acccatcctt cgttttcgga     600
cctcagaact ttgatgaaga cgtcactaag aaactaaatg aaacttgtga aattatcaat     660
ggtttattac atgctccatt tgacaccaaa gtcgaaaaga ctcacttcag tcaattcatt     720
gatgttcgtg atgtcgccaa aactcacgtt ttgggtttcc aaaaagatga attaatcaac     780
caaagattgt tattatgtaa cggcgccttc tctcaacaag atattgttaa tgtatttaat     840
gaagatttcc cagagttaaa aggccaattc ccaccagaag ataaggacac cgatttaaac     900
aaaggtgtaa caggttgtaa aattgataat gaaaagacta aaaaattatt agcatttgaa     960
tttactcctt tccataaaac aattcatgac actgtctatc aaattttaca taagaaggt    1020 agagtttaa                                                             1029

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
agaagtcaag acattgctga t                                                21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
taacttatca gcaatgtctt g                                                21

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
```

```
gcttcaatta tggatccaca taga                                          24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
ttgtctatgt ggatccataa ttga                                          24

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
aatgcttatg aagatgtcgt t                                             21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
agcagtaacg acatcttcat a                                             21

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
gaagacgtca ctgaaaaact aaat                                          24

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
ttcatttagt ttttcagtga cgtc                                          24

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
gatgtcgcca aagcacacgt tttg                                          24

<210> SEQ ID NO 12
<211> LENGTH: 24
<212> TYPE: DNA
<213> ORGANISM: Artificial Sequence
```

```
<220> FEATURE:
<223> OTHER INFORMATION: Primer

<400> SEQUENCE: 12
acccaaaacg tgtgctttgg cgac                                              24

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
ggcgccttct ctctgcaaga tatt                                              24

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
aacaatatct tgcagagaga aggc                                              24

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
ccacatagaa ataatgatcc a                                                 21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
tggatcatta tttctatgtg g                                                 21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
tatgaaaatg tcgttactgc t                                                 21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
acaataagca gtaacgacat t                                                 21
```

```
<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
actatccacc caggtttcgt t                                              21

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
tccgaaaacg aaacctgggt g                                              21

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
ctaaatggta cttgtgaaat t                                              21

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
aatttcacaa gtaccattta g                                              21

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
aagactcact tctgtcaatt c                                              21

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
atcaatgaat tgacagaagt g                                              21
```